United States Patent
Wu et al.

(10) Patent No.: US 11,284,856 B2
(45) Date of Patent: Mar. 29, 2022

(54) METHOD FOR DETECTING VASCULAR OBSTRUCTION AND SYSTEM USING THE SAME

(71) Applicant: Industrial Technology Research Institute, Hsinchu (TW)

(72) Inventors: Guo-Zua Wu, Taichung (TW); Yuan-Mao Hung, Nantou County (TW); Ken-Tsu Hu, Taipei (TW)

(73) Assignee: Industrial Technology Research Institute, Hsinchu (TW)

(*) Notice: Subject to any disclaimer, the term of this patent is extended or adjusted under 35 U.S.C. 154(b) by 298 days.

(21) Appl. No.: 16/731,047

(22) Filed: Dec. 31, 2019

(65) Prior Publication Data

US 2021/0196231 A1 Jul. 1, 2021

(51) Int. Cl.
*A61B 8/00* (2006.01)
*A61B 8/08* (2006.01)
*G06T 7/262* (2017.01)

(52) U.S. Cl.
CPC .......... *A61B 8/0891* (2013.01); *A61B 8/4272* (2013.01); *A61B 8/4444* (2013.01); *G06T 7/262* (2017.01); *G06T 2207/20056* (2013.01); *G06T 2207/30101* (2013.01)

(58) Field of Classification Search
CPC .... A61B 8/0891; A61B 8/4272; A61B 8/4444
See application file for complete search history.

(56) References Cited

U.S. PATENT DOCUMENTS

| 5,957,950 A * | 9/1999 | Mockros | A61M 25/104 |
| | | | 606/194 |
| 9,715,885 B2 * | 7/2017 | Sugiyama | A61B 5/024 |
| 2015/0327837 A1 | 11/2015 | Qi et al. | |

FOREIGN PATENT DOCUMENTS

| CN | 101779966 | 7/2010 |
| CN | 201444530 | * 12/2014 |
| CN | 106682442 | 5/2017 |
| CN | 109124688 | 1/2019 |
| TW | I498099 | 9/2015 |

OTHER PUBLICATIONS

"Office Action of Taiwan Counterpart Application", dated Jun. 1, 2020, p. 1-p. 9.

* cited by examiner

*Primary Examiner* — Joseph M Santos Rodriguez
(74) *Attorney, Agent, or Firm* — JCIPRNET (57) ABSTRACT

A method for detecting vascular obstruction and a system using the same are provided. The method includes steps of: detecting a blood vessel through a probe to generate a reference signal before the blood vessel is obstructed, wherein the probe is configured to transmit or receive ultrasonic waves; detecting the blood vessel through the probe to generate a detection signal; performing Fourier transformation on the reference signal to generate a reference power spectrum, and performing Fourier transformation on the detection signal to generate a detection power spectrum; transforming the reference power spectrum into a reference time-frequency spectrogram, and transforming the detection power spectrum into a detection time-frequency spectrogram; judging a similarity between the reference time-frequency spectrogram and the detection time-frequency spectrogram, and judging whether the blood vessel is obstructed or not according to the similarity.

20 Claims, 8 Drawing Sheets

METHOD FOR DETECTING VASCULAR OBSTRUCTION AND SYSTEM USING THE SAME

TECHNICAL FIELD

The disclosure relates to a method for detecting vascular obstruction and a system using the same.

BACKGROUND

With the gradual change of the population type into the aging society, people's demands for health care and home care gradually increase. In the foreseeable future, medical resources will be increasingly insufficient to support all patients. For example, a patient with hemodialysis demands needs to go to a hospital from time to time to check whether an arteriovenous graft (AVG) of the patient may be obstructed or not. When the number of patients is excessive, medical personnel are often on the verge of burnout. As such, the waiting time of the patients is increased, and the medical quality is reduced.

Therefore, people skilled in the pertinent art are dedicated to developing an arteriovenous obstruction detecting method for home use.

SUMMARY

The disclosure provides a method for detecting vascular obstruction and a system using the same, and whether a blood vessel of a user is obstructed or not may be detected through the portable system.

A system for detecting vascular obstruction according to an embodiment of the disclosure includes a probe, a transceiver, and a processor. The probe is configured to transmit or receive ultrasonic waves. The transceiver is coupled to the probe. A storage medium stores a plurality of modules. The processor is coupled to the storage medium and the transceiver and accesses and executes the modules, wherein the modules include a data collection module and an operation module. The data collection module detects a blood vessel through the probe to generate a reference signal before the blood vessel is obstructed, and detects the blood vessel through the probe to generate a detection signal. The operation module performs Fourier transformation on the reference signal to generate a reference power spectrum, performs Fourier transformation on the detection signal to generate a detection power spectrum, transforms the reference power spectrum into a reference time-frequency spectrogram, transforms the detection power spectrum into a detection time-frequency spectrogram, judges a similarity between the reference time-frequency spectrogram and the detection time-frequency spectrogram, and judges whether the blood vessel is obstructed or not according to the similarity.

In an embodiment of the disclosure, the above operation module transforms the reference time-frequency spectrogram into a first binarized image, transforms the detection time-frequency spectrogram into a second binarized image, performs exclusive or operation on the first binarized image and the second binarized image to generate an operation result, and judges the similarity according to a global maximum value of the operation result.

In an embodiment of the disclosure, the above operation module judges that the blood vessel is not obstructed in response to the similarity being greater than a threshold, and judges that the blood vessel is obstructed in response to the similarity being less than or equal to the threshold.

In an embodiment of the disclosure, the above operation module performs Fourier transformation on the reference signal or the detection signal according to Hamming windows.

In an embodiment of the disclosure, the above system further includes a fixing member. The fixing member is disposed on a signal transmission path between the blood vessel and the probe, wherein the fixing member is configured to fix the probe.

In an embodiment of the disclosure, the above fixing member includes an interface between a first medium and a second medium, wherein an included angle between the interface and the blood vessel is not 0 degree.

In an embodiment of the disclosure, the above second medium is in contact with skin wrapping the blood vessel, and the acoustic impedance of the second medium is between the first acoustic impedance of the first medium and the second acoustic impedance of the blood vessel.

In an embodiment of the disclosure, the above second medium is in contact with the skin wrapping the blood vessel, and the acoustic impedance of the second medium is between the first acoustic impedance of the probe and the second acoustic impedance of the blood vessel.

In an embodiment of the disclosure, the above transceiver includes a signal transmitting circuit coupled to the probe and transmitting a first ultrasonic signal through the probe, a signal receiving circuit coupled to the probe and receiving a second ultrasonic signal corresponding to the first ultrasonic signal through the probe, a signal operation circuit coupled to the signal transmitting circuit and the signal receiving circuit, commanding the signal transmitting circuit to transmit the first ultrasonic signal and transforming the second ultrasonic signal into an electric signal, a demodulation circuit coupled to the signal operation circuit and demodulating the electric signal to generate one of the reference signal and the detection signal, and a recording circuit coupled to the demodulation circuit and the processor and storing one of the reference signal and the detection signal to the storage medium through the processor.

In an embodiment of the disclosure, the above blood vessel is an arteriovenous graft.

A method for detecting vascular obstruction according to an embodiment of the disclosure includes: detecting a blood vessel through a probe to generate a reference signal before the blood vessel is obstructed, wherein the probe is configured to transmit or receive ultrasonic waves; detecting the blood vessel through the probe to generate a detection signal; performing Fourier transformation on the reference signal to generate a reference power spectrum, and performing Fourier transformation on the detection signal to generate a detection power spectrum; transforming the reference power spectrum into a reference time-frequency spectrogram, and transforming the detection power spectrum into a detection time-frequency spectrogram; judging a similarity between the reference time-frequency spectrogram and the detection time-frequency spectrogram; and judging whether the blood vessel is obstructed or not according to the similarity.

In an embodiment of the disclosure, the above step of judging the similarity between the reference time-frequency spectrogram and the detection time-frequency spectrogram includes: transforming the reference time-frequency spectrogram into a first binarized image; transforming the detection time-frequency spectrogram into a second binarized image; performing exclusive or operation on the first binarized image and the second binarized image to generate an operation result; and judging the similarity according to a global maximum value of the operation result.

In an embodiment of the disclosure, the above step of judging whether the blood vessel is obstructed or not according to the similarity includes: judging that the blood vessel is not obstructed in response to the similarity being greater than a threshold; and judging that the blood vessel is obstructed in response to the similarity being less than or equal to the threshold.

In an embodiment of the disclosure, the above step of performing Fourier transformation on the reference signal to generate the reference power spectrum, and performing Fourier transformation on the detection signal to generate the detection power spectrum includes: performing Fourier transformation on the reference signal or the detection signal according to Hamming windows.

In an embodiment of the disclosure, the above method further includes: disposing a fixing member on a signal transmission path between the blood vessel and the probe, wherein the fixing member is configured to fix the probe.

In an embodiment of the disclosure, the above fixing member includes an interface between a first medium and a second medium, wherein an included angle between the interface and the blood vessel is not 0 degree.

In an embodiment of the disclosure, the above second medium is in contact with skin wrapping the blood vessel, and the acoustic impedance of the second medium is between the first acoustic impedance of the first medium and the second acoustic impedance of the blood vessel.

In an embodiment of the disclosure, the above second medium is in contact with the skin wrapping the blood vessel, and the acoustic impedance of the second medium is between the first acoustic impedance of the probe and the second acoustic impedance of the blood vessel.

In an embodiment of the disclosure, the above step of detecting the blood vessel by the probe to generate the detection signal includes: sending a first ultrasonic signal through the probe; receiving a second ultrasonic signal corresponding to the first ultrasonic signal through the probe; transforming the second ultrasonic signal into an electric signal; and demodulating the electric signal to generate the detection signal.

In an embodiment of the disclosure, the above blood vessel is an arteriovenous graft.

In view of the foregoing, one or more embodiments of the disclosure may provide the user-portable system to be worn on the wrist of a user. The system may detect the state of the blood vessels of the user and judge whether any blood vessel is obstructed or not. Thus, the user may be effectively protected from being harmed due to obstruction of the blood vessel.

DETAILED DESCRIPTION OF DISCLOSED EMBODIMENTS

To make the content of the disclosure more comprehensible, embodiments are described below as examples according to which the disclosure can indeed be implemented. Wherever possible, the same reference numbers are used in the drawings and the description to refer to the same or like parts, components or steps.

Figure 1:
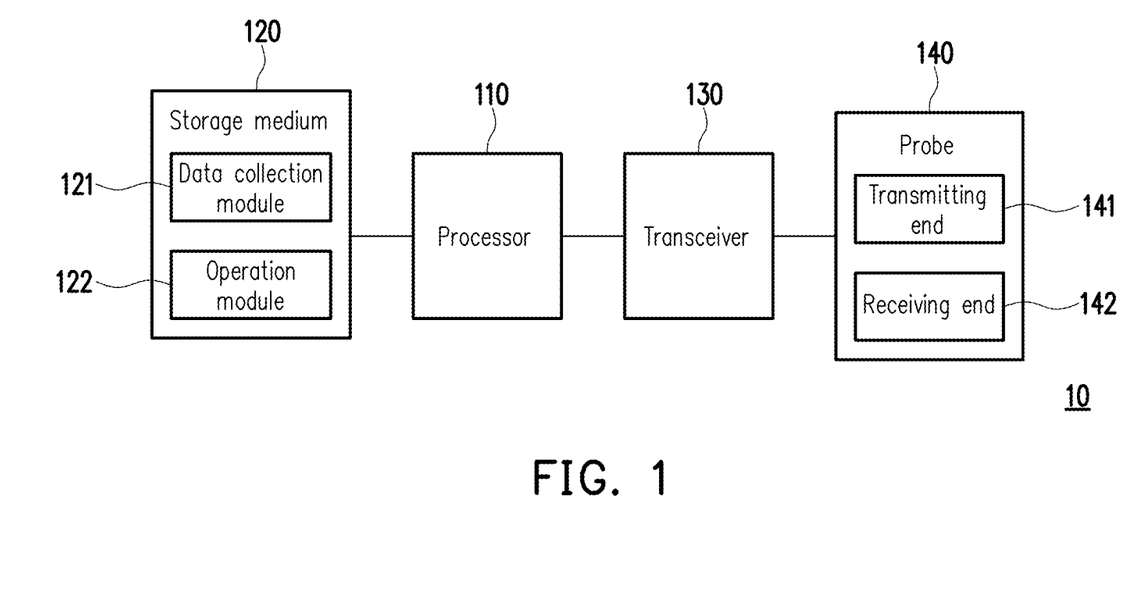
FIG. 1 is a schematic diagram of a system for detecting vascular obstruction according to an embodiment of the disclosure.

FIG. 1 is a schematic diagram of a system 10 for detecting vascular obstruction according to an embodiment of the disclosure. The system 10 includes a processor 110, a storage medium 120, a transceiver 130 and a probe 140.

The processor 110 is, for example, a central processing unit (CPU), or other programmable general-purpose or special-purpose micro control unit (MCU), microprocessor, digital signal processor (DSP), programmable controller, application specific integrated circuit (ASIC), graphics processing unit (GPU), image signal processor (ISP), image processing unit (IPU), arithmetic logic unit (ALU), complex programmable logic device (CPLD), field programmable logic array (FPGA) or other similar elements or a combination of the above elements. The processor 110 may be coupled to the storage medium 120 and the transceiver 130, and accesses and executes a plurality of modules and various application programs which are stored in the storage medium 120.

The storage medium 120 is, for example, any type of fixed or removable random access memory (RAM), read-only memory (ROM), flash memory, hard disk drive (HDD), solid state drive (SSD), or similar elements or a combination thereof, and is configured to store the plurality of modules or various application programs that may be executed by the processor 110. In the present embodiment, the storage medium 120 may store the plurality of modules including a data collection module 121 and an operation module 122, and the functions of the modules will be described later.

Figure 2:
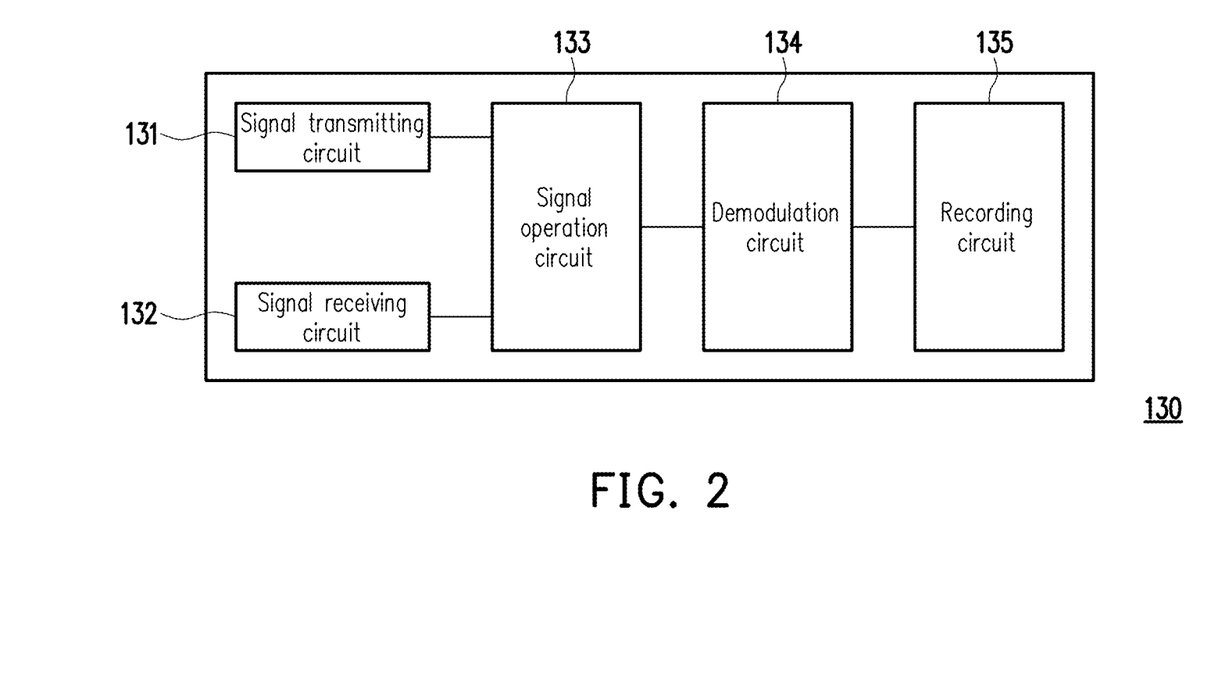
FIG. 2 is a schematic diagram of a transceiver according to an embodiment of the disclosure.

The transceiver 130 may be coupled to the probe 140 and is configured to control the probe 140 to transmit a signal or demodulate a signal received by the probe 140. FIG. 2 is a schematic diagram of the transceiver 130 according to an embodiment of the disclosure. The transceiver 130 may include a signal transmitting circuit 131, a signal receiving circuit 132, a signal operation circuit 133, a demodulation circuit 134, and a recording circuit 135.

The signal transmitting circuit 131 may be coupled to the probe 140 and transmits a first ultrasonic signal through the probe 140. The signal receiving circuit 132 may be coupled to the probe 140 and receives a second ultrasonic signal corresponding to the first ultrasonic signal through the probe 140.

The signal operation circuit 133 may be coupled to the signal transmitting circuit 131, the signal receiving circuit 132 and the demodulation circuit 134. The signal operation circuit 133 may command the signal transmitting circuit 131 to transmit the first ultrasonic signal through the probe 140. In addition, the signal operation circuit 133 may receive the second ultrasonic signal from the signal receiving circuit 132 and transform the second ultrasonic signal into an electric signal.

The demodulation circuit 134 may be coupled to the signal operation circuit 133 and the recording circuit 135. The demodulation circuit 134 may receive the electric signal corresponding to the second ultrasonic signal from the signal operation circuit 133 and demodulate the electric signal to generate a demodulation signal. Specifically, the demodulation circuit 134 may demodulate the electric signal through the Doppler effect to generate the demodulation signal.

The recording circuit 135 may be coupled to the demodulation circuit 134 and the processor 110. The recording circuit 135 may transmit the demodulation signal from the demodulation circuit 134 to the storage medium 120 through the processor 110 to be stored.

With reference to FIG. 1 again, the probe 140 may include a transmitting end 141 and a receiving end 142. The probe 140 may transmit the first ultrasonic signal through the transmitting end 141. After the first ultrasonic signal reaches an object (for example: a blood vessel of a user) to be detected by the system 10, the object may reflect some or all of the first ultrasonic signal to generate the second ultrasonic signal. The probe 140 may receive the second ultrasonic signal through the receiving end 142. The processor 110 may judge the state of the detected object through the first ultrasonic signal and the second ultrasonic signal.

Figure 3A:
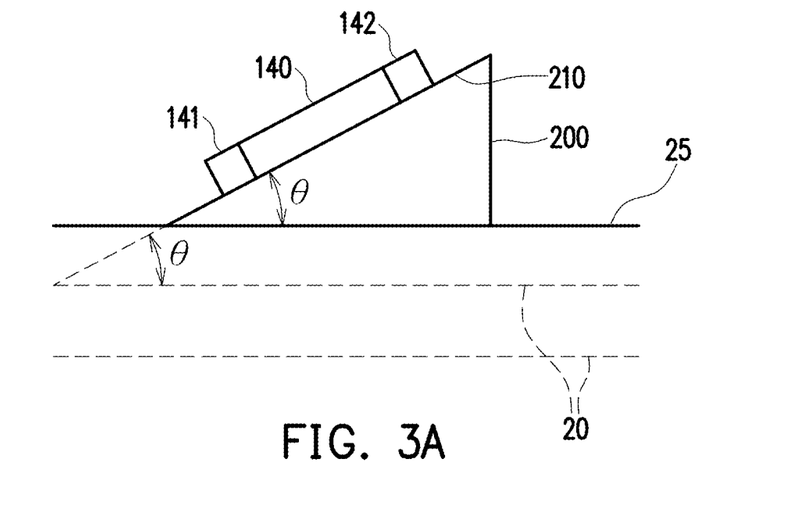
FIG. 3A is a schematic diagram of one form of a fixing member according to an embodiment of the disclosure.

The system 10 further includes a fixing member 200 configured to fix the probe 140 (or the system 10) to the wrist (or limbs or a trunk, etc., to which the disclosure is not limited) of the user. FIG. 3A is a schematic diagram of one form of a fixing member 200 according to an embodiment of the disclosure. As shown in FIG. 3A, it is assumed that the system 10 is configured to detect whether the blood vessel 20 of the user is obstructed or not, and the probe 140 may be fixed to skin 25 covering the blood vessel 20 by the fixing member 200 such that the fixing member 200 is disposed on a signal transmission path between the blood vessel 20 and the probe 140, wherein the signal transmission path is a transmission path of the first ultrasonic signal or the second ultrasonic signal.

In the present embodiment, the fixing member 200 may include an interface 210 between a medium of the fixing member 200 and a medium of the probe 140, wherein an included angle θ between the interface 210 and the blood vessel 20 is not 0 degree. In another embodiment, an included angle θ is less than 90 degrees. In other words, the interface 210 may be obliquely disposed on the skin 25, and the interface 210 may not be parallel to the blood vessel 20, as shown in FIG. 3A. The medium of the fixing member 200 may be in contact with the skin 25 wrapping the blood vessel 20, and the acoustic impedance of the medium of the fixing member 200 is between the acoustic impedance of the probe 140 and the acoustic impedance of the blood vessel 20 (or the skin 25). More specifically, the acoustic impedance of the probe 140 corresponds to a sound velocity of about 2500 meters/second, the acoustic impedance of the blood vessel 20 corresponds to a sound velocity of about 1540 meters/second, and the sound velocity corresponding to the acoustic impedance of the medium of the fixing member 200 is between about 1540 meters/second and 2500 meters/second. In other words, the acoustic impedance of the blood vessel 20 is greater than the acoustic impedance of the medium of the fixing member 200, and the acoustic impedance of the medium of the fixing member 200 is greater than the acoustic impedance of the probe 140.

Figure 3B:
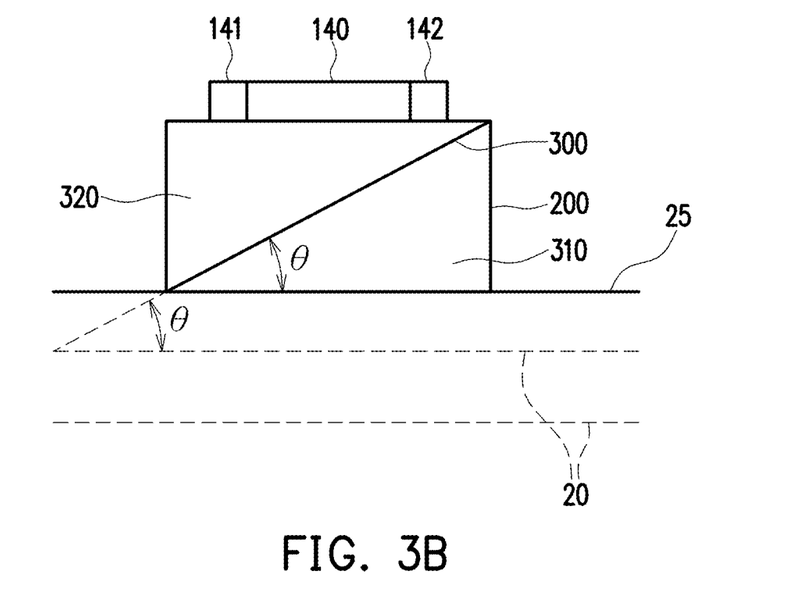
FIG. 3B is a schematic diagram of another form of a fixing member according to an embodiment of the disclosure.

FIG. 3B is a schematic diagram of another form of a fixing member 200 according to an embodiment of the disclosure. In the present embodiment, the fixing member 200 may be composed of two mediums, wherein the two mediums are a medium 310 and a medium 320 respectively. An interface 300 is disposed between the medium 310 and the medium 320, and an included angle θ between the interface 300 and the blood vessel 20 is not 0 degree. In another embodiment, an included angle θ is less than 90 degrees. In other words, the interface 300 may be obliquely disposed on the skin 25, and the interface 300 may not be parallel to the blood vessel 20, as shown in FIG. 3B. The medium 310 of the fixing member 200 may be in contact with the skin 25 wrapping the blood vessel 20, and the medium 320 of the fixing member 200 may be in contact with the probe 140. The acoustic impedance of the medium 310 is between the acoustic impedance of the medium 320 and the acoustic impedance of the blood vessel 20 (or the skin 25). More specifically, the acoustic impedance of the blood vessel 20 is greater than the acoustic impedance of the medium 310, and the acoustic impedance of the medium 310 is greater than the acoustic impedance of the medium 320.

After the user wears the probe 140 on the wrist, the data collection module 121 may detect the blood vessel 20 through the probe 140 before the blood vessel 20 is obstructed to generate a reference signal corresponding to an initial state of the blood vessel 20. The data collection module 121 may generate the reference signal based on the Doppler effect according to the first ultrasonic signal and the second ultrasonic signal. The reference signal will be used as a reference for the processor 110 to judge the state of the blood vessel 20. If the difference between a detection signal detected by the probe 140 and the reference signal is too large, the processor 110 may judge that the blood vessel 20 may have been obstructed.

Figure 4:
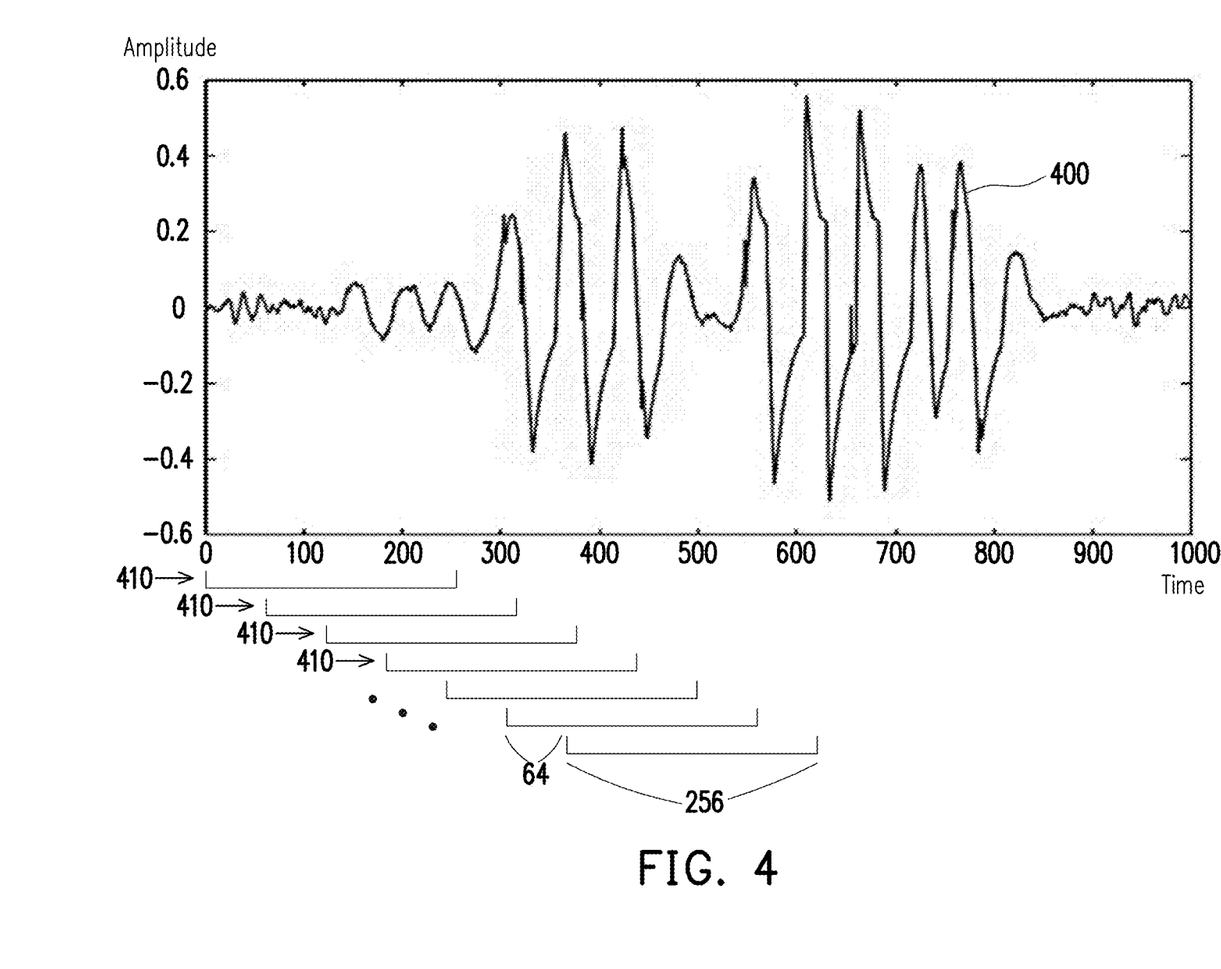
FIG. 4 is a schematic diagram of a reference signal according to an embodiment of the disclosure.

After the reference signal is generated, the operation module 122 may perform Fourier transformation on the reference signal to generate a reference power spectrum. FIG. 4 is taken as an example, and FIG. 4 is a schematic diagram of the reference signal 400 according to an embodiment of the disclosure. The operation module 122 may be partitioned into a plurality of hamming windows 410 in a time axis direction to perform Fourier transformation on the reference signal 400. Adjacent Hamming windows contain overlapping regions. In the present embodiment, each Hamming window 410 may include 256 sampling points, and 192 sampling points are overlapped between the adjacent Hamming windows, though the disclosure is not limited thereto. The operation module 122 may perform Fourier transformation on the reference signal to generate the reference power spectrum according to a formula (1) shown below, wherein p is reference power, f is a frequency, W is a function of the Hamming windows, X is a function of the reference signal, Δt is sampling time of the reference signal and m is the size of the Hamming windows (or the number of the sampling points). In the present embodiment, m is equal to 256.

$$p(f) = (\Delta t)^2 \cdot |\Sigma_{n<1}^m W(t) \cdot X(t) \cdot e^{-2\pi i f n}|^2 \quad (1)$$

Figure 5:
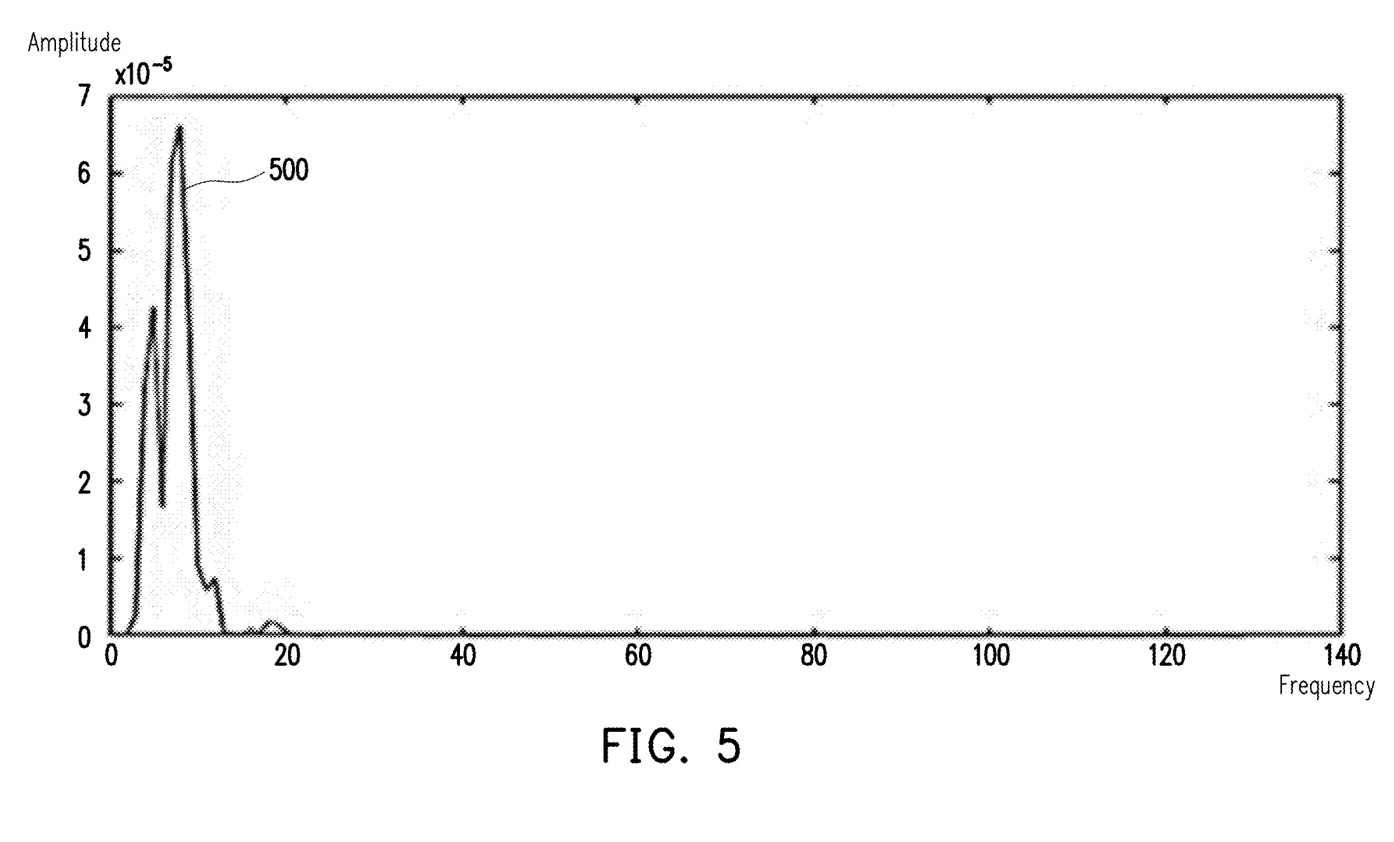
FIG. 5 is a schematic diagram of a reference power spectrum according to an embodiment of the disclosure.

The operation module 122 may perform Fourier transformation on the reference signal 400 according to the formula (1) to generate the reference power spectrum 500 as shown in FIG. 5. FIG. 5 is a schematic diagram of the reference power spectrum 500 according to an embodiment of the disclosure. After the reference power spectrum 500 is generated, the operation module 122 may further transform the reference power spectrum 500 into a corresponding reference time-frequency spectrogram (or referred to a spectral waterfall, voiceprint, voicegram, etc.). The operation module 122 may store the reference time-frequency spectrogram corresponding to the reference power spectrum 500 into the storage medium 120.

When the user wears the probe 140 on the wrist, the probe 140 may continuously detect the state of the blood vessel 20 of the user. In one embodiment, the blood vessel 20 is, for example, an arteriovenous graft. Specifically, the data collection module 121 may detect the blood vessel 20 through the probe 140 to generate the detection signal. The data collection module 121 may generate the detection signal according to a detection result of the probe 140 based on the Doppler effect. After the detection signal is generated, the operation module 122 may perform Fourier transformation on the detection signal to generate a detection power spectrum. The process for generating the detection power spectrum according to the detection signal is similar to the process for generating the reference power spectrum according to the reference signal, and therefore, the descriptions thereof are omitted herein.

After the detection power spectrum is generated, the operation module 122 may further transform the detection power spectrum into a corresponding detection time-frequency spectrogram. The operation module 122 may store the detection time-frequency spectrogram corresponding to the detection power spectrum in the storage medium 120.

After the detection time-frequency spectrogram is generated, the operation module 122 may judge the similarity between the reference time-frequency spectrogram and the detection time-frequency spectrogram, and judge whether the blood vessel 20 is obstructed or not according to the similarity. Specifically, the operation module 122 may transform the reference time-frequency spectrogram and the detection time-frequency spectrogram into a first binarized image and a second binarized image, respectively, and perform exclusive or operation on the first binarized image and the second binarized image to generate an operation result. After the operation result is generated, the operation module 122 may judge the similarity according to a global maximum value of the operation result. If the global maximum value of the operation result is higher, the similarity between the first binarized image corresponding to the reference signal and the second binarized image corresponding to the detection signal is higher. The operation module 122 may perform exclusive or operation on the first binarized image and the second binarized image according to a formula (2) shown below, wherein z is a similarity, a is a value (a may be equal to 0 or 1) of a point in the first binarized image, b is a value (b may be equal to 0 or 1) of a point in the second binarized image, L1 is the length of the first binarized image and L2 is the length of the second binarized image.

$$z(\varepsilon)=\sum_{x=1}^{L1}\sum_{y=1}^{L2}a(x+\varepsilon,y)(\text{Xor})b(x,y) \quad (2)$$

The operation module 122 may judge that the blood vessel 20 is not obstructed in response to the similarity between the first binarized image and the second binarized image being greater than a specific threshold, and judge that the blood vessel 20 is obstructed in response to the similarity being less than or equal to the specific threshold. The magnitude of the threshold may be adjusted according to usage requirements.

Figure 6:
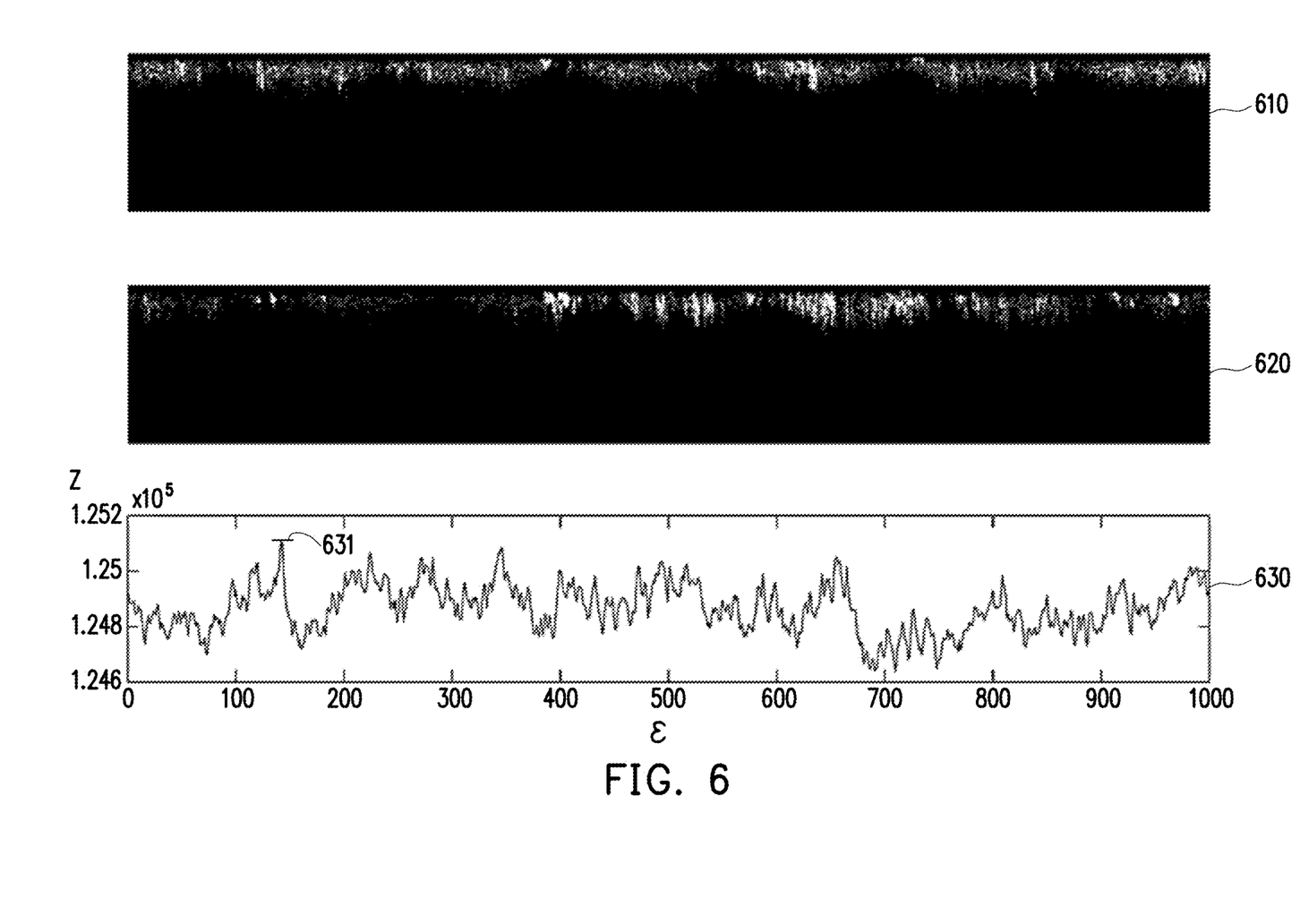
FIG. 6 is a schematic diagram of a first binarized image, a second binarized image, and a similarity curve when a blood vessel is not obstructed according to an embodiment of the disclosure.
Figure 7:
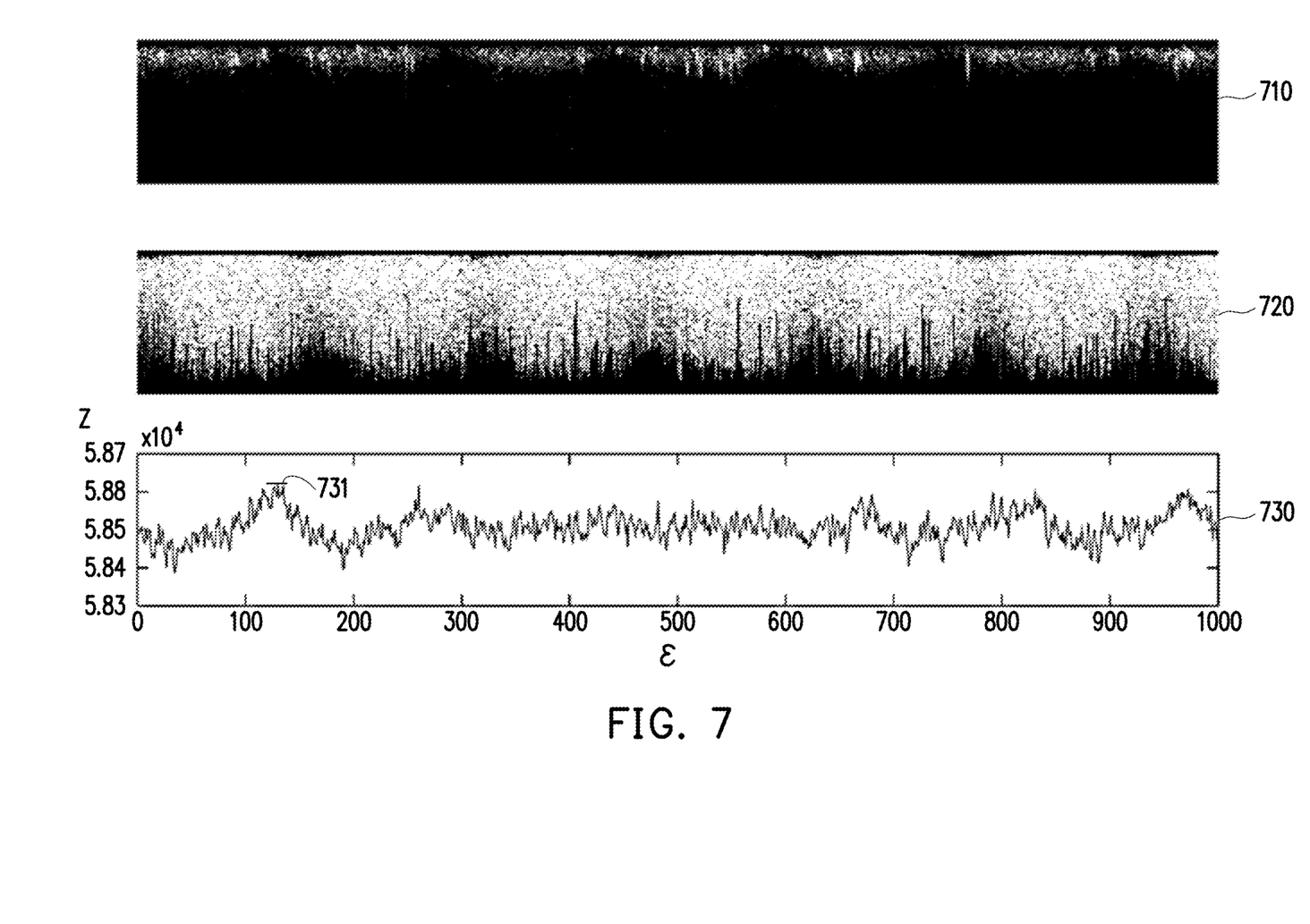
FIG. 7 is a schematic diagram of a first binarized image, a second binarized image, and a similarity curve when a blood vessel is obstructed according to another embodiment of the disclosure.

FIG. 6 and FIG. 7 are taken as examples. FIG. 6 is a schematic diagram of a first binarized image 610, a second binarized image 620, and a similarity curve 630 when the blood vessel 20 is not obstructed according to an embodiment of the disclosure, and FIG. 7 is a schematic diagram of a first binarized image 710, a second binarized image 720, and a similarity curve 730 when the blood vessel 20 is obstructed according to another embodiment of the disclosure. With reference to FIG. 6 and FIG. 7, the operation module 122 may perform exclusive or operation on the first binarized image 610 and the second binarized image 620 according to the formula (2), thereby generating the similarity curve 630 corresponding to the similarity between the first binarized image 610 and the second binarized image 620. The operation module 122 may judge that the blood vessel 20 is not obstructed in response to a global maximum value 631 of the similarity curve 630 being greater than a threshold. In addition, the operation module 122 may perform exclusive or operation on the first binarized image 710 and the second binarized image 720 according to the formula (2), thereby generating the similarity curve 730 corresponding to the similarity between the first binarized image 710 and the second binarized image 720. The operation module 122 may judge that the blood vessel 20 is obstructed in response to a global maximum value 731 of the similarity curve 730 being less than or equal to the threshold.

Figure 8:
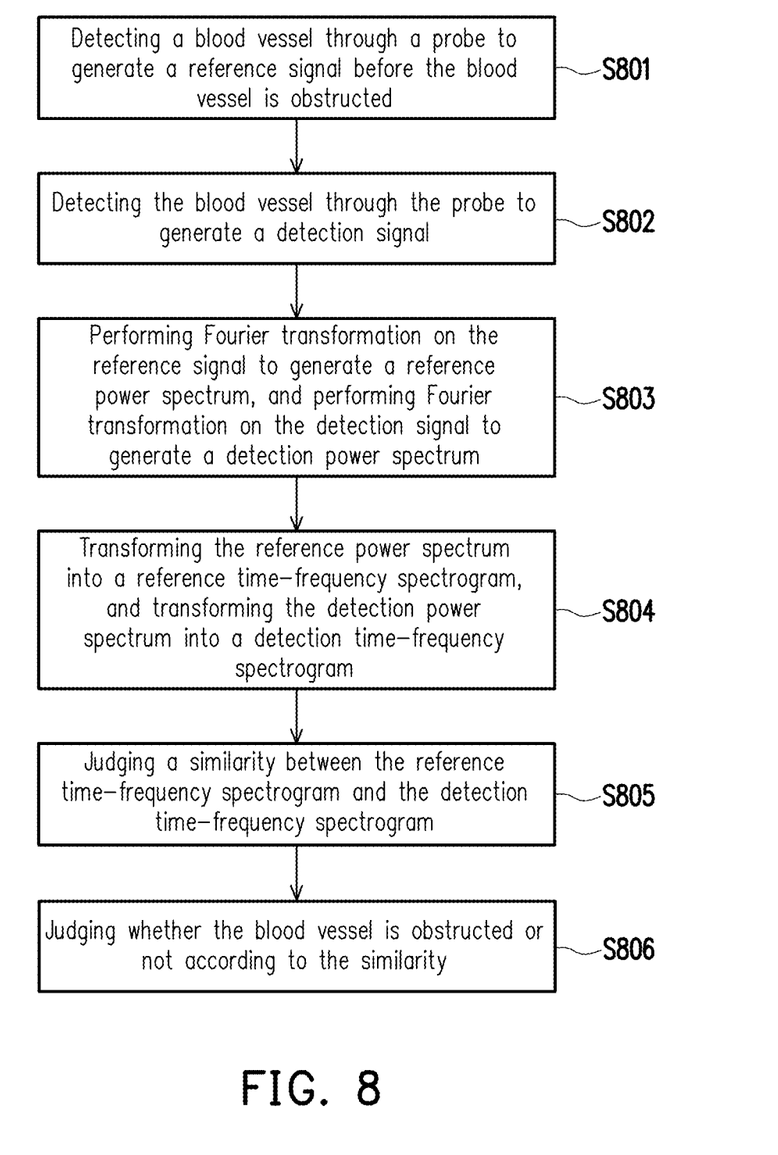
FIG. 8 is a flowchart of a method for detecting vascular obstruction according to an embodiment of the disclosure.

FIG. 8 is a flowchart of a method for detecting vascular obstruction according to an embodiment of the disclosure. The method is implemented by the system 10 shown in FIG. 1. In step S801, a blood vessel 20 is detected through a probe 140 before being obstructed so as to generate a reference signal, wherein the probe 140 is configured to transmit or receive ultrasonic waves. In step S802, the blood vessel 20 is detected through the probe 140 to generate a detection signal. In step S803, Fourier transformation is performed on the reference signal to generate a reference power spectrum, and Fourier transformation is performed on the detection signal to generate a detection power spectrum. In step S804, the reference power spectrum is transformed into a reference time-frequency spectrogram, and the detection power spectrum is transformed into a detection time-frequency spectrogram. In step S805, the similarity between the reference time-frequency spectrogram and the detection time-frequency spectrogram is judged. In step S806, whether the blood vessel 20 is obstructed or not is judged according to the similarity.

In summary, the disclosure may provide the user-portable system to be worn on the wrist of the user. The fixing member may fix the probe to the skin of the user. When the user wears the system for the first time, the system may detect the state of the blood vessel of the user before the blood vessel is obstructed through ultrasonic waves to serve as the reference signal. By Fourier transformation and binarization, the system may visualize the state of the blood vessel. When the system detects that the state of the blood vessel of the user is not matched with the reference signal through the images, the system may judge that the blood vessel of the user is obstructed. The system may prompt the user to go to the hospital for examination through an external output device. Thus, the user may be effectively prevented from being harmed due to obstruction of the blood vessel.

What is claimed is:

1. A system for detecting vascular obstruction, comprising:
 a probe configured to transmit or receive ultrasonic waves;
 a transceiver coupled to the probe;
 a storage medium storing a plurality of modules; and a processor coupled to the storage medium and the transceiver and accessing and executing the plurality of modules, wherein the plurality of modules comprises:
  a data collection module configured to detect a blood vessel through the probe to generate a reference signal before the blood vessel is obstructed, and detect the blood vessel through the probe to generate a detection signal; and
  an operation module configured to perform Fourier transformation on the reference signal to generate a reference power spectrum, perform Fourier transformation on the detection signal to generate a detection power spectrum, transform the reference power spectrum into a reference time-frequency spectrogram, transform the detection power spectrum into a detection time-frequency spectrogram, judge a similarity between the reference time-frequency spectrogram and the detection time-frequency spectrogram, and judge whether the blood vessel is obstructed or not according to the similarity.

2. The system according to claim 1, wherein the operation module transforms the reference time-frequency spectrogram into a first binarized image, transforms the detection time-frequency spectrogram into a second binarized image, performs exclusive or operation on the first binarized image and the second binarized image to generate an operation result, and judges the similarity according to a global maximum value of the operation result.

3. The system according to claim 1, wherein the operation module judges that the blood vessel is not obstructed in response to the similarity being greater than a threshold, and judges that the blood vessel is obstructed in response to the similarity being less than or equal to the threshold.

4. The system according to claim 1, wherein the operation module performs Fourier transformation on the reference signal or the detection signal according to Hamming windows.

5. The system according to claim 1, further comprising:
  a fixing member disposed on a signal transmission path between the blood vessel and the probe, wherein the fixing member is configured to fix the probe.

6. The system according to claim 5, wherein the fixing member comprises an interface between a first medium and a second medium, and an included angle between the interface and the blood vessel is not 0 degree.

7. The system according to claim 6, wherein the second medium is in contact with skin wrapping the blood vessel, and acoustic impedance of the second medium is between first acoustic impedance of the first medium and second acoustic impedance of the blood vessel.

8. The system according to claim 6, wherein the second medium is in contact with skin wrapping the blood vessel, and the acoustic impedance of the second medium is between first acoustic impedance of the probe and second acoustic impedance of the blood vessel.

9. The system according to claim 1, wherein the transceiver comprises:
  a signal transmitting circuit coupled to the probe and transmitting a first ultrasonic signal through the probe;
  a signal receiving circuit coupled to the probe and receiving a second ultrasonic signal corresponding to the first ultrasonic signal through the probe;
  a signal operation circuit coupled to the signal transmitting circuit and the signal receiving circuit, commanding the signal transmitting circuit to transmit the first ultrasonic signal, and transforming the second ultrasonic signal into an electric signal;
  a demodulation circuit coupled to the signal operation circuit and demodulating the electric signal to generate one of the reference signal and the detection signal; and
  a recording circuit coupled to the demodulation circuit and the processor and storing one of the reference signal and the detection signal to the storage medium through the processor.

10. The system according to claim 1, wherein the blood vessel is an arteriovenous graft.

11. A method for detecting vascular obstruction, comprising:
  detecting a blood vessel through a probe to generate a reference signal before the blood vessel is obstructed, wherein the probe is configured to transmit or receive ultrasonic waves;
  detecting the blood vessel through the probe to generate a detection signal;
  performing Fourier transformation on the reference signal to generate a reference power spectrum, and performing Fourier transformation on the detection signal to generate a detection power spectrum;
  transforming the reference power spectrum into a reference time-frequency spectrogram, and transforming the detection power spectrum into a detection time-frequency spectrogram;
  judging a similarity between the reference time-frequency spectrogram and the detection time-frequency spectrogram; and
  judging whether the blood vessel is obstructed or not according to the similarity.

12. The method according to claim 11, wherein the step of judging the similarity between the reference time-frequency spectrogram and the detection time-frequency spectrogram comprises:
  transforming the reference time-frequency spectrogram into a first binarized image;
  transforming the detection time-frequency spectrogram into a second binarized image;
  performing exclusive or operation on the first binarized image and the second binarized image to generate an operation result; and
  judging the similarity according to a global maximum value of the operation result.

13. The method according to claim 11, wherein the step of judging whether the blood vessel is obstructed or not according to the similarity comprises:
  judging that the blood vessel is not obstructed in response to the similarity being greater than a threshold; and
  judging that the blood vessel is obstructed in response to the similarity being less than or equal to the threshold.

14. The method according to claim 11, wherein the step of performing Fourier transformation on the reference signal to generate the reference power spectrum, and performing Fourier transformation on the detection signal to generate the detection power spectrum comprises:
  performing Fourier transformation on the reference signal or the detection signal according to Hamming windows.

15. The method according to claim 11, further comprising:
  placing a fixing member on a signal transmission path between the blood vessel and the probe, wherein the fixing member is configured to fix the probe.

16. The method according to claim 15, wherein the fixing member comprises an interface between a first medium and a second medium, and an included angle between the interface and the blood vessel is not 0 degree.

17. The method according to claim 16, wherein the second medium is in contact with skin wrapping the blood vessel, and acoustic impedance of the second medium is between first acoustic impedance of the first medium and second acoustic impedance of the blood vessel.

18. The method according to claim 16, wherein the second medium is in contact with skin wrapping the blood vessel, and acoustic impedance of the second medium is between first acoustic impedance of the probe and second acoustic impedance of the blood vessel.

19. The method according to claim 11, wherein the step of detecting the blood vessel by the probe to generate the detection signal comprises:
   sending a first ultrasonic signal through the probe;
   receiving a second ultrasonic signal corresponding to the first ultrasonic signal through the probe;
   transforming the second ultrasonic signal into an electric signal; and
   demodulating the electric signal to generate the detection signal.

20. The method according to claim 11, wherein the blood vessel is an arteriovenous graft.

* * * * *